US011925197B2

(12) United States Patent
Clarke et al.

(10) Patent No.: US 11,925,197 B2
(45) Date of Patent: Mar. 12, 2024

(54) BETA-CASEINS AND GUT MICROBIOTA

(71) Applicant: THE A2 MILK COMPANY LIMITED, Auckland (NZ)

(72) Inventors: Andrew John Clarke, Auckland (NZ); Catherine Mary Babidge, Auckland (NZ); Jiayi Ni, Shanghai (CN)

(73) Assignee: THE A2 MILK COMPANY LIMITED, Auckland (NZ)

( * ) Notice: Subject to any disclaimer, the term of this patent is extended or adjusted under 35 U.S.C. 154(b) by 0 days.

(21) Appl. No.: 16/333,939

(22) PCT Filed: Sep. 30, 2016

(86) PCT No.: PCT/NZ2016/050161
§ 371 (c)(1),
(2) Date: Mar. 15, 2019

(87) PCT Pub. No.: WO2018/063008
PCT Pub. Date: Apr. 5, 2018

(65) Prior Publication Data
US 2020/0008458 A1 Jan. 9, 2020

(51) Int. Cl.
*A23L 33/19* (2016.01)
*A23C 9/13* (2006.01)
*A23C 9/15* (2006.01)
*A23C 13/14* (2006.01)
*A23C 15/12* (2006.01)
*A23C 19/09* (2006.01)
*A61K 35/20* (2006.01)
*A61K 38/01* (2006.01)
*A23J 1/20* (2006.01)

(52) U.S. Cl.
CPC ............ *A23L 33/19* (2016.08); *A23C 9/1307* (2013.01); *A23C 9/1512* (2013.01); *A23C 13/14* (2013.01); *A23C 15/12* (2013.01); *A23C 19/0917* (2013.01); *A61K 35/20* (2013.01); *A61K 38/018* (2013.01); *A23J 1/202* (2013.01)

(58) Field of Classification Search
CPC ..... A23L 33/19; A23C 9/1307; A23C 9/1512; A23C 13/14; A23C 15/12; A23C 19/0917; A61K 35/20; A61K 38/018; A61K 38/1709; A61K 38/17; A23J 1/202; A23J 1/20; A23V 2002/00; A23V 2200/3202; A23V 2250/54246; A61P 1/00
See application file for complete search history.

(56) References Cited

U.S. PATENT DOCUMENTS 10,568,933 B2 * 2/2020 Clarke ...................... A61P 3/10
10,702,580 B2 * 7/2020 Clarke ...................... A61P 1/16

FOREIGN PATENT DOCUMENTS

| CN | 103918792 A | 7/2014 | |
|---|---|---|---|
| WO | 96/14577 A1 | 5/1996 | |
| WO | 96/36239 A1 | 11/1996 | |
| WO | 02/19832 A1 | 3/2002 | |
| WO | 2014/193248 A1 | 12/2014 | |
| WO | 2015/005804 A1 | 1/2015 | |
| WO | WO-2015005804 A1 * | 1/2015 | ............. A61K 35/20 |
| WO | 2015/026245 A1 | 2/2015 | |

OTHER PUBLICATIONS

Jianqin, 2016, Nutrition Journal, 15-35 (Year: 2016).*
Website: https://www.dictionary.com/browse/providing, 6 pages, retrieved on Jan. 6, 2021 (Year: 2021).*
Website: https://web.archive.org/web/20140114000607/https://www.a2milk.com.au/, 1 page, 2014 (Year: 2014).*
KV Satyanarayana, The hype over branded A2 milk, 6 pages, 2018 (Year: 2018).*
Website: https://web.archive.org/web/20140114000648/http://a2milk.com.au/about-a2-milk.php, 1 page 2014 (Year: 2014).*
Ho, European Journal of Clinical Nutrition (2014) 68, 994-1000 (Year: 2014).*
Jianqin, Nutrition Journal (2016) 15:35, pp. 1-16 (Year: 2016).*
Website: https://www.merriam-webster.com/dictionary/altered, 1 page, retrieved on Dec. 15, 2021 (Year: 2021).*
Trinchese et (Journal of Nutritional Biochemistry, 2015, 26, 1136-1146) (Year: 2015).*
Rios-Covian et al (Frontiers in Microbiology, Feb. 2016, vol. 7, article 185, pp. 1-9) (Year: 2016).*
Sadler et al (infant, 2013, vol. 9, issue 5, pp. 173-176) (Year: 2013).*
Document 1 (See A2 and A2 milk protein—frequently asked Q&As, 2021) (Year: 2021).*
Binder et al., Role of colonic short-chain fatty acid transport in diarrhea, Annu. Rev. Physiol., 72:297-313 (2010).
Blouin et al., Butyrate elicits a metabolic switch in human colon cancer cells by targeting the pyruvate dehydrogenase complex, Int. J. Cancer, 128:2591-2601 (2011).
Breuer et al., Rectal irrigation with short-chain fatty acids for distal ulcerative colitis, Preliminary report Dig. Dis. Sci., 36:185-187 (1991).
Donohoe et al., The microbiome and butyrate regulate energy metabolism and autophagy in the mammalian colon, Cell Metab., 13:517-526 (2011).
Gao et al. Butyrate improves insulin sensitivity and increases energy expenditure in mice, Diabetes, 58:1509-1517 (2009).

(Continued)

*Primary Examiner* — Sudhakar Katakam

(74) *Attorney, Agent, or Firm* — MARSHALL, GERSTEIN & BORUN LLP

(57) ABSTRACT

Improving the balance of beneficial gut microbiota of an animal by providing a composition containing beta-casein, wherein at least 75% by weight of the beta-casein is a beta-casein variant that has a proline at position 67 of the beta-casein amino acid sequence.

7 Claims, No Drawings

(56) References Cited

OTHER PUBLICATIONS

Hamer et al., Review article: the role of butyrate on colonic function, Aliment. Pharmacol. Ther., 27:104-119 (2008).
Harig et al., Treatment of diversion colitis with short-chain-fatty acid irrigation, N. Engl. J. Med., 320:23-28 (1989).
Hermes et al., Casein glycomacropeptide in the diet may reduce *Escherichia coli* attachment to the intestinal mucosa and increase the intestinal lactobacilli of early weaned piglets after an enterotoxigenic *E. coli* K88 challenge, British Journal of Nutrition, 109:1001-1012 (2013).
Ho et al., Comparative effects of A1 versus A2 beta-casein on gastrointestinal measures: a blinded randomised cross-over pilot study, European Journal of Clinical Nutrition, 68:994-1000 (2014).
Hu et al., Activation of the AMP activated protein kinase by short-chain fatty acids is the main mechanism underlying the beneficial effect of a high fiber diet on the metabolic syndrome, Med. Hypotheses, 74:123-126 (2010).
International Preliminary Report on Patentability for corresponding International Application No. PCT/NZ2016/050161, dated Apr. 11, 2019.
Jianqin et al., Effects of milk containing only A2 beta casein versus milk containing both A1 and A2 beta casein proteins on gastrointestinal physiology, symptoms of discomfort, and cognitive behavior of people with self-reported intolerance to traditional cows' milk, Nutrition Journal, published online, 15:1-16 (2016).
Sabatino et al., Oral butyrate for mildly to moderately active Crohn's disease, Aliment Pharmacol. Ther., 22:789-794 (2005).
Scharlau et al., Mechanisms of primary cancer prevention by butyrate and other products formed during gut flora-mediated fermentation of dietary fibre, Mutat. Res., 682:39-53 (2009).
Scheppach W., Treatment of distal ulcerative colitis with short-chain fatty acid enemas. A placebo-controlled trial. German-Austrian SCFA Study Group, Dig. Dis. Sci., 41:2254-2259 (1996).
Tang et al., G-protein-coupled receptor for shortchain fatty acids suppresses colon cancer, Int. J. Cancer, 128:847-856 (2011).
Vernia et al., Short-chain fatty acid topical treatment in distal ulcerative colitis, Aliment Pharmacol. Ther., 9:309-313 (1995).
Wurth et al., Physiological relevance of food grade microcapsules: Impact of milk protein based microcapsules on inflammation in mouse models for inflammatory bowel diseases, Molecular Nutrition & Food Research, 59:1629-1634 (2015).

* cited by examiner

BETA-CASEINS AND GUT MICROBIOTA

TECHNICAL FIELD

The invention relates to the milk protein beta-casein and improving the balance of beneficial gut microbiota in animals. In particular, the invention relates to milk and milk derived food products having a beta-casein composition that comprises predominantly A2 beta-casein or related beta-casein variants. The applicant has found that the consumption of milk containing the A2 variant of beta-casein is associated with beneficially altered faecal levels of short-chain fatty acids and therefore positively influences the composition of gut microbiota.

BACKGROUND OF THE INVENTION

Gut microbiota (or gut flora) consists of a complex community of microorganisms that live in the digestive tract of animals. One of the ways gut microorganisms benefit the host is by the fermentation of undigested carbohydrates and the subsequent production of short-chain fatty acids (SCFAs). The most important of these SCFAs are acetic acid, propanoic acid and butanoic acid (sometimes referred to as acetates, propionates and butyrates). It can be generalised that acetates are metabolised by the muscle tissue, propionates by the liver, and butyrates by the colonic epithelium. SCFAs constitute approximately two-thirds of the colonic anion concentration (70-130 mmol/l), mainly as acetate, propionate, and butyrate, and are produced in nearly constant molar ratio 60:25:15. Among their various properties, SCFAs are readily absorbed by intestinal mucosa, are relatively high in caloric content, are metabolised by colonocytes and epatocytes, stimulate sodium and water absorption in the colon and are trophic to the intestinal mucosa. Butyrate has been studied for its role in nourishing the colonic mucosa and in the prevention of cancer of the colon, by promoting cell differentiation, cell-cycle arrest and apoptosis of transformed colonocytes, and inhibiting the enzyme histone deacetylase and decreasing the transformation of primary to secondary bile acids as a result of colonic acidification. Therefore, a greater increase in SCFA production and potentially a greater delivery of SCFAs, specifically butyrate, to the distal colon may result in a protective effect.

All infants are initially colonised by large numbers of *E. coli* and *streptococci*. During the first week of life, these bacteria create a reducing environment favourable for the subsequent bacterial succession of species belonging to the genera *Bifidobacterium, Bacteroides, Clostridium* and *Ruminococcus*. The microbiota of breast-fed babies becomes dominated by bifidobacteria, whereas the microbiota of formula-fed babies tends to be more diverse with high numbers of *enterobacteriaceae, enterococci, bifidobacteria, bacteroides* and *clostridia*.

The composition of the microbiota stays unstable until it matures at the age of approximately 3-4 years. Colonisation of the gut has two major benefits. First, the microbiota educate the immune system and increase tolerance to microbial immunodeterminants. Second, the microbiota act as a metabolic organ that can break down otherwise indigestible food components, degrade potentially toxic food compounds like oxalate, and synthesise certain vitamins and amino acids. Each individual has a unique microbiome the composition of which is influenced by the host genotype and physiology, the colonisation history, environmental factors, food, and drugs (e.g. antibiotics).

The composition of the gut flora also changes over time and when the diet changes. Gut flora can be changed by following a long-term diet. People having microbiota that is predominantly Bacteroides (from a diet based on high levels of protein and fat) who change their dietary patterns to a diet based largely on high levels of carbohydrates may develop a Prevotella enterotype in the long term. Thus, long-term dietary interventions may allow modulation of an individual's enterotype to improve health.

In the last few decades, it has become apparent that colonic levels of SCFAs might play a key role in the prevention and treatment of metabolic syndrome, bowel disorders and certain types of cancer.[1-7] In some clinical studies, SCFA administration positively influenced the treatment of ulcerative colitis, Crohn's disease, and antibiotic associated diarrhoea.[8-13]

Milk, mainly bovine milk, consumed in populations throughout the world, is a major source of protein in human diets and therefore influences gut microbiota. Bovine milk typically comprises around 30 grams per litre of protein. Caseins make up the largest component (80%) of that protein, and beta-caseins make up about 37% of the caseins. In the past two decades the body of evidence implicating casein proteins, especially beta-caseins, in a number of health disorders has been growing.

The beta-caseins can be categorised as A1 beta-casein and A2 beta-casein. These two proteins are the predominant beta-caseins in the bovine milk consumed in most human populations. A1 beta-casein differs from A2 beta-casein by a single amino acid. A histidine amino acid is located at position 67 of the 209 amino acid sequence of A1 beta-casein, whereas a proline is located at the same position of A2 beta-casein. This single amino acid difference is, however, critically important to the enzymatic digestion of beta-caseins in the gut. The presence of histidine at position 67 allows a protein fragment comprising seven amino acids, known as beta-casomorphin-7 (BCM-7), to be produced on enzymatic digestion. Thus, BCM-7 is a digestion product of A1 beta-casein. In the case of A2 beta-casein, position 67 is occupied by a proline which hinders cleavage of the amino acid bond at that location. Thus, BCM-7 is not a digestion product of A2 beta-casein.

Other beta-casein variants, such as the B, C, F, G and H variants, also have histidine at position 67, whereas variants in addition to the A2 variant, such as the A3, D, E and I variants, have proline at position 67. But these variants are found only in very low levels, or not found at all, in milk from cows of European origin. Thus, in the context of this invention, the term A1 beta-casein may refer to any beta-casein having histidine at position 67, and the term A2 beta-casein may refer to any beta-casein having proline at position 67.

BCM-7 is an opioid peptide and can bind to and activate opioid receptors throughout the body. BCM-7 has the ability to cross the gastrointestinal wall and enter circulation enabling it to influence systemic and cellular activities via opioid receptors. The applicant and others have previously determined an adverse association between the consumption of A1 beta-casein found in milk or milk products and type I diabetes,[14] coronary heart disease,[15] neurological disorders,[16] inflammation of the bowel,[17] the symptoms of lactose intolerance[18] and blood glucose levels.[19]

In its ongoing investigations into links between beta-casein variants and biological response in humans, the applicant has now found a positive association between A2 beta-casein and gut microbiota. The association is based on the SCFA profile of faeces of individuals who have consumed milk containing only the A2 variant of beta-casein.

It is therefore an object of the invention to provide a method for improving levels of beneficial gut microbiota in humans and other animals, or to at least provide a useful alternative to existing methods.

SUMMARY OF THE INVENTION

In a first aspect of the invention there is provided a method of improving the levels of beneficial gut microbiota of an animal by ingesting a composition containing beta-casein or by providing to an animal a composition containing beta-casein, wherein at least 75% by weight of the beta-casein is a beta-casein variant that has a proline at position 67 of the beta-casein amino acid sequence.

In certain embodiments of the invention the beta-casein variant is A2 beta-casein, A3 beta-casein, D beta-casein, E beta-casein or I beta-casein. In preferred embodiments the beta-casein variant is A2 beta-casein. The amount of A2 beta-casein may be any amount in the range of 75% to 100% by weight of the beta-casein, for example at least 90% or even 100%.

In certain embodiments of the invention improved gut microbiota is assessed by measuring the levels of one or more short-chain fatty acids in a faecal sample. The one or more short-chain fatty acids may be selected from the group comprising acetic acid, propanoic acid and butanoic acid, or an ester thereof.

In certain embodiments of the invention the composition is milk or a milk product. The milk may be fresh milk, milk powder, liquid milk reconstituted from powder, skim milk, homogenised milk, condensed milk, evaporated milk, pasteurised milk, or non-pasteurised milk. The milk product may be infant formula, cream, yoghurt, quark, cheese, butter, ice cream, or any other milk product.

In a second aspect of the invention there is provided a composition for improving the levels of beneficial gut microbiota in an animal which composition contains beta-casein, wherein at least 75% by weight of the beta-casein is a beta-casein variant that has a proline at position 67 of the beta-casein amino acid sequence.

In another aspect of the invention there is provided the use of milk in the manufacture of a composition for improving the levels of beneficial gut microbiota in an animal where the milk contains beta-casein and where at least 75% by weight of the beta-casein is a beta-casein variant that has a proline at position 67 of the beta-casein amino acid sequence.

In a further aspect of the invention there is provided a method of promoting the growth of beneficial bacteria in the gut of an animal comprising the ingestion by the animal of a composition containing beta-casein or by providing to the animal a composition containing beta-casein, wherein at least 75% by weight of the beta-casein is a beta-casein variant that has a proline at position 67 of the beta-casein amino acid sequence.

In certain embodiments of the invention promoting the growth of beneficial bacteria in the gut avoids or reduces the risk of cancer, liver disease, systemic infections, inflammatory and autoimmune diseases, obesity and metabolic syndrome, and neurological disorders.

DETAILED DESCRIPTION

The invention relates to a composition containing the protein beta-casein and its use for improving gut microbiota in animals, specifically humans. Importantly, the beta-casein is preferably the A2 variant of beta-casein, or makes up at least 75% by weight of the total beta-casein variants present in the composition.

The term "gut microbiota" or "gut biota" or "gut microflora" or "gut flora" is intended to mean the complex community of microorganisms that live in the digestive tracts of humans and other animals.

The term "beta-casomorphin-7" or "BCM-7" refers to the protein fragment Tyr-Pro-Phe-Pro-Gly-Pro-Ile, a heptapeptide produced on enzymatic digestion of bovine beta-casein variants that have a histidine, rather than a praline, at position 67 of the amino acid sequence.

The term "short-chain fatty acid" or "SCFA" refers to a fatty acid having an aliphatic tail comprising less than six carbon atoms, and includes formic acid (methanoic acid), acetic acid (ethanoic acid), propionic acid, butyric acid (butanoic acid), isobutyric acid (2-methylpropanoic acid), valeric acid (pentanoic acid) and isovaleric acid (3-methylbutanoic acid). Acetic acid, propionic acid and butyric acid are the predominant SCFAs in the body.

The importance of the predominance of the A2 variant in the composition is due to the fact that the applicant has shown that there is a direct link between the A2 variant and beneficially altered levels of specific SCFAs in faecal samples obtained from humans. The applicant's finding that the ingestion of a mixture of A1 beta-casein and A2 beta-casein does not provide the same level of improved gut microbiota as the ingestion of a comparable amount of A2 beta-casein (i.e. no A1 beta-casein in the diet) is considered to be due, at least in part, to the production of BCM-7 in the gut from A1 beta-casein, but not from A2 beta-casein. BCM-7 causes inflammation in the gut, has an adverse immune response and increases intestinal transit time. Thus, BCM-7 alters the gut envionment and is therefore likely to affect the gut microbiota off-setting the nutritional benefits of milk.

The composition of the invention is responsible for beneficially altering the intestinal levels of bacteria from any one or more of the following genera *Bifidobacterium, Bacteroides, Clostridium* and *Ruminococcus*.

High levels of some bacteria, for example clostridia, produce high levels of propionate which has been implicated in neurodevelopmental disorders such as autism. Individuals with autism often have impaired carbohydrate digestion and absorption. Some studies suggest that gastrointestinal symptoms correlate with the severity of autistic symptoms in patients and this is associated with alterations in intestinal bacteria.

Within the human gastrointestinal microbiota exists a complex ecosystem of approximately 300 to 500 bacterial species. At birth, the entire intestinal tract is sterile. The infant's gut is first colonised by maternal and environmental bacteria during birth and continues to be populated through feeding and other contacts. Factors known to influence colonisation include gestational age, mode of delivery (vaginal birth v. assisted delivery), diet (breast milk v. formula), level of sanitation, and exposure to antibiotics. The intestinal microbiota of newborns is characterised by low diversity and a relative dominance of the phyla *Proteobacteria* and *Actinobacteria*. Thereafter, the microbiota becomes more diverse with the emergence of the dominance of Firmicutes and Bacteroidetes, which characterises the adult microbiota. By the end of the first year of life, the microbial profile is distinct for each infant. By the age of 2.5 years, the microbiota fully resembles the microbiota of an adult in terms of composition. This period of maturation of the microbiota may be critical.

Following infancy, the composition of the intestinal microflora remains relatively constant until later life. Three different enterotypes have been described in the adult microbiome. These distinct enterotypes are dominated by *Prevotella*, *Ruminococcus*, and *Bacteroides*, and their appearance seems to be independent of sex, age, nationality and body mass index.

Concentrations of $10^{12}$ CFU/mL or greater may be found in the colon and are comprised mainly of anaerobes such as *Bacteroides*, *Porphyromonas*, *Bifidobacterium*, *Lactobacillus*, and *Clostridium*, with anaerobic bacteria outnumbering aerobic bacteria by a factor of 100 to 1000:1.

Since the primary, if not only, source of beta-caseins in the diet of most human populations is milk or products derived from milk, and since most milk consumed contains a mixture of the A1 and A2 variants of beta-casein only, the consumption of milk (or products made from such milk) having a high content of the A2 variant will necessarily mean that the consumption of the A1 variant is low. Thus, if the only dietary source of beta-casein contains the A2 variant and no other variant, the dietary intake of the A1 variant is eliminated and the adverse effect of BCM-7 on gut health can therefore also be expected to be eliminated.

Accordingly, the invention of this application is based on the reduction or elimination of A1 beta-casein in the diet, and the promotion of A2 beta-casein. This is achieved by ensuring that the beta-casein in beta-casein containing food compositions, especially milk and milk products, is predominantly or even exclusively A2 beta-casein, or at least one of the beta-casein variants that does not produce BCM-7 on digestion.

Ideally, the beta-casein in the composition is 100% A2 beta-casein. However, gut health may be enhanced by any composition where the beta-casein is predominantly A2 beta-casein, for example, any amount between 75% by weight and 100%, including but not limited to 80%, 90%, 95%, 98% and 99% by weight.

The composition of the invention is typically milk, but may also be any milk-derived product such as cream, yoghurt, quark, cheese, butter, or ice cream. The composition may also be a non-milk product containing beta-casein that has been obtained from milk. The composition may be beta-casein itself, or may be prepared from beta-casein, which beta-casein may be in solid form such as powder or granules or in the form of a solid cake.

While the milk may be obtained from any mammal, including humans, goats, pigs and buffalo, in preferred embodiments of the invention the milk is bovine milk.

The milk may be in the form of fresh milk, milk powder, liquid milk reconstituted from a powder, skim milk, homogenised milk, condensed milk, evaporated milk, pasteurised milk or non-pasteurised milk, or any other form of milk.

The composition of the invention is applicable for consumption by humans primarily, but it should be appreciated that the health benefit is also relevant for some other animals such as cats, dogs and other domestic animals.

Support for the invention is found in Example 1 which describes a trial where subjects were assigned to consume milk containing both A1 and A2 beta-caseins (referred to as the A1/A2 beta-casein containing product) and milk containing only A2 beta-casein (referred to as the A2 beta-casein only product). Gut microbiota was assessed by measuring faecal concentrations of acetic acid, propanoic acid and butanoic acid, as well as total SCFAs. The results are shown in Table 2. The mixed effect ANOVA results show significant differences between the two milk product sequences especially for acetic acid ($P=0.0052$), butanoic acid ($P=0.0001$) and total SCFAs ($P=0.0009$).

The consumption of the A2 beta-casein only product led to elevated levels of acetic acid and butanoic acid (and total SCFA levels) compared to the consumption of the A1/A2 beta-casein containing product and compared to the baseline. In contrast, there was no difference observed in levels of propionic acid. Higher levels of acetic acid and butanoic acid, but not propionic acid, are considered to indicate healthy levels of gut microbiota.

Since the SCFA levels measured on consumption of the A1/A2 beta-casein containing product are approximately the same as the baseline measurements, it is thought that the consumption of A2 beta-casein exerts a positive effect on gut health or A1 beta-casein negates the positives effects conferred by other components of milk.

These studies represent the first clear scientific evidence of a link between A2 beta-casein consumption and improved gut microbiota. Through the applicant's finding, it is clear that the consumption of beta-caseins that produce BCM-7 on digestion should be avoided. In practical terms, the benefits of the invention can be achieved for large populations by sourcing milk having a beta-casein content that is predominantly A2 beta-casein and producing products derived from that milk, and making that milk and those products available for the purpose of improving, enhancing or maintaining gut health.

The milk of cows can be tested for the relative proportions of A1 beta-casein and A2 beta-casein. Alternatively, cows can be genetically tested for their ability to produce milk containing A1 beta-casein (or other variants capable of producing BCM-7) or tested for their ability to produce milk containing A2 beta-casein (or other variants incapable of producing BCM-7) or a combination of both. These techniques are well-known.

The present invention provides a solution that is comparatively easy to manage, i.e. avoidance of milk or milk products that contain A1 beta-casein and ensuring that milk and milk products in the diet contain beta-casein that is predominantly A2 beta-casein, preferably 100% A2 beta-casein.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following example. It will be appreciated that the invention as claimed is not intended to be limited in any way by this example.

EXAMPLE

Example 1

Milk Trial and Faecal SCFAs Measurement

Study Design

The study was conducted in accordance with the Declaration of Helsinki as amended in Seoul 2008 and was approved by the ethics committee of the Shanghai Nutrition Society (approval number: SNSIRB #2014[002]). The study was registered with ClinicalTrials.gov (identifier: NCT02406469). All subjects provided written informed consent prior to inclusion in the study. This was a single-site, double-blind, randomised, controlled, 2×2 cross-over study designed to evaluate the effects of milk containing only the A2 beta-casein type versus milk containing the A1 and A2 beta-casein types on serum levels of immune response markers in correlation to symptoms of intolerance. After a screening visit at which the subjects underwent full clinical evaluations and qualitative tests for urinary galactose, eligible subjects entered a 2-week washout period. The subjects then entered intervention period 1 in which they received milk containing only the A2 beta-casein variant (the A2 beta-casein only product) or milk containing both A1 and A2 beta-casein variants (the A1/A2 beta-casein containing product) according to the randomisation scheme for 2 weeks. After a second 2-week washout period, the subjects entered intervention period 2 in which they received the opposite milk product. Visits were scheduled at the start of each intervention period and at Days 7 and 14 in each intervention period. The subjects were contacted by telephone during each washout period. The study was conducted at the Department of Gastroenterology, Xin Hua Hospital Affiliated to Shanghai Jiao Tong University School of Medicine (Shanghai, China).

Interventions

The A2 beta-casein only product and the A1/A2 beta-casein containing product were provided by A2 Infant Nutrition Limited (Auckland, New Zealand), and were distributed to the study site by S.P.R.I.M. China (Shanghai) Consulting Co., Ltd. (SPRIM China). Staff at SPRIM China repackaged and labelled all of the products to ensure the investigators and subjects were blinded to which product they received in each intervention period. In each intervention period, the subjects were instructed to consume 250 ml of milk after 2 meals per day for 14 days. Subjects used a diary to record milk intake and adherence to each intervention. Used and unused cartons were collected at each visit to evaluate compliance with the interventions and to confirm that the blinding was intact. Subjects were randomised, with stratification by gender, to sequence 1 (A1/A2→A2) or sequence 2 (A2→A1/A2) according to the allocation number filed in sealed envelopes. The allocation was based on a computer-generated list prepared by SPRIM China.

The A2 beta-casein only product contained (per 100 ml) 271 kJ energy, 3.1 g protein, 3.6 g fat, 5.0 g carbohydrate, 48 mg sodium, 150 mg potassium, and 117 mg calcium. The ratio of A1 beta-casein to A2 beta-casein was approximately 40:60 in the A1/A2 beta-casein containing product, as confirmed by ultra performance liquid chromatography and mass spectrometry. Both products were identical and contained the same amount of protein.

The consumption of dairy products other than those provided was prohibited during the study. Subjects were permitted to consume non-dairy milk products (no dairy products were consumed) during each washout period.

Subjects

The inclusion criteria were as follows: male or female; age 25-68 years; irregular milk consumption (as documented using a food frequency questionnaire); self-reported intolerance to commercial milk; self-reported mild to moderate digestive discomfort after milk consumption; and normal electrocardiograms (ECG) and blood pressure during quiet respiration. Subjects were enrolled if they: agreed not to take any medication, nutritional supplements, or other dairy products, including acidophilus milk, during the study; were willing to comply with all of the requirements and procedures; provided signed informed consent; agreed not to participate in another interventional clinical research study during the present study; did not meet any of the exclusion criteria; and fully understood the nature, objective, benefit, and the potential risks and side effects of the study. Subjects were recruited via advertisements placed on noticeboards at community hospitals. Summary statistics are shown in Table 1.

TABLE 1

Evaluation of Baseline Characteristics Mean (SD) or Frequency (%)

| Study Group | Sequence A1-A2 (n = 22) | | Sequence A2-A1 (n = 23) | | Overall | | ANOVA (p-value) |
|---|---|---|---|---|---|---|---|
| Gender Male | 10 | (45.5%) | 11 | (47.8%) | 21 | (46.7%) | / |
| Female | 12 | (54.5%) | 12 | (52.2%) | 24 | (53.3%) | |
| Age (year) | 45.7 | (12.3) | 47.5 | (15.6) | 46.6 | (14.0) | 0.664 |
| Weight (kg) | 72.4 | (19.9) | 66.7 | (14.3) | 69.5 | (17.3) | 0.272 |
| Height (cm) | 167.5 | (9.4) | 166.4 | (8.0) | 166.9 | (8.6) | 0.695 |
| BMI (kg/m$^2$) | 25.4 | (4.6) | 24.0 | 3.7 | 24.6 | 4.2 | 0.226 |
| Body Temperature (° C.) | 36.9 | (0.1) | 36.8 | (0.2) | 36.8 | (0.2) | 0.207 |
| Diastolic pressure (mmHg) | 76.1 | (5.2) | 75.5 | (6.5) | 75.8 | (5.8) | 0.748 |
| Systolic pressure (mmHg) | 124.6 | (6.7) | 121.2 | (8.8) | 122.9 | (7.9) | 0.145 |

Statistical Analysis

The Kolmogorov-Smirnov Test was used to assess the normality of continuous variables. Non-normally distributed variables were subjected to square-root or log transformation to approximate a normal distribution. Baseline characteristics are presented descriptively as means±standard deviation (SD) or the number (percent) of subjects. Faecal concentrations of SCFAs were analysed using mixed-effects analysis of variance in which the allocated intervention and intervention period were included as fixed effects, and subject was included as a random effect nested within the study sequence (i.e., sequence 1, A1/A2→A2; sequence 2, A2→A1/A2). To investigate whether there were differences between the two interventions in the mean values for each endpoint, and whether the mean values changed during the study periods, Type III tests of fixed effects were used to tests the effects of the interventions and study periods. Additionally, contrast tests were performed to compare the mean values for each product. The presence of a carry-over effect was evaluated using the interaction Intervention× Period. If this interaction was not significant, data from both periods were evaluated. If the interaction was significant, only data from intervention period 1 were used.

Faecal SCFA Biomarkers

Results of faecal laboratory tests are presented in Table 2. There were no intervention period or sequence effects for any of the laboratory variables. However, the baseline value was a significant covariate for all laboratory variables. As shown in Table 2, there were significant differences between the two milk products in terms of the faecal concentrations of acetic add (P=0.0052), butanoic add (P=0.0001), and total short-chain fatty acids (SCFAs) (P=0.0009). No differences in propionic add levels were observed.

TABLE 2

Results of serum and fecal laboratory tests

| | Sequence 1[a] | | | | Sequence 2[b] | |
| --- | --- | --- | --- | --- | --- | --- |
| | Period 1 | | Period 2 | | Period 1 | |
| Variable | BL | PI | BL | PI | BL | PI |
| Acetic acid (%) | 0.42 ± 0.15 | 0.42 ± 0.15 | 0.40 ± 0.14 | 0.46 ± 0.11 | 0.39 ± 0.19 | 0.46 ± 0.19 |
| Propanoic acid (%) | 0.18 ± 0.07 | 0.18 ± 0.07 | 0.17 ± 0.07 | 0.17 ± 0.07 | 0.17 ± 0.09 | 0.19 ± 0.13 |
| Butanoic acid (%) | 0.17 ± 0.07 | 0.16 ± 0.07 | 0.16 ± 0.07 | 0.20 ± 0.08 | 0.17 ± 0.09 | 0.23 ± 0.09 |
| Total SCFA (%) | 0.76 ± 0.24 | 0.76 ± 0.24 | 0.72 ± 0.24 | 0.83 ± 0.19 | 0.73 ± 0.33 | 0.88 ± 0.33 |

| | | Sequence 2[b] | | Mixed-effects ANOVA | | |
| --- | --- | --- | --- | --- | --- | --- |
| | | Period 2 | | | | P- |
| | Variable | BL | PI | Estimate[c] | SD | value[d] |
| | Acetic acid (%) | 0.39 ± 0.17 | 0.36 ± 0.11 | −0.0667 | 0.0226 | 0.0052 |
| | Propanoic acid (%) | 0.18 ± 0.09 | 0.17 ± 0.07 | −0.006[e] | 0.0187 | 0.7504 |
| | Butanoic acid (%) | 0.17 ± 0.08 | 0.16 ± 0.05 | −0.0515 | 0.0122 | 0.0001 |
| | Total SCFA (%) | 0.74 ± 0.28 | 0.69 ± 0.18 | −0.1289 | 0.03609 | 0.0009 |

[a]Sequence 1: A1/A2→A2
[b]Sequence 2: A2→A1/A2
[c]A1/A2-A2
[d]Values in bold are statistically significant at P < 0.05
[e]Because the variable was non-normally distributed, mixed-effects ANOVA was performed using the square root-transformed values
[f]Because the variable was non-normally distributed, mixed-effects ANOVA was performed using the log-transformed values
ANOVA analysis of variance,
BL baseline,
PI postintervention (i.e., after 2 weeks of each intervention),
SD standard deviation,
SCFA short-chain fatty acids Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

REFERENCES

1. Hu G. X., Chen G. R., Xu H., Ge R. S., Lin J., Activation of the AMP activated protein kinase by short-chain fatty acids is the main mechanism underlying the beneficial effect of a high fiber diet on the metabolic syndrome. Med. Hypotheses. 74: 123-126, 2010.
2. Gao Z., Yin J., Zhang J., Ward R. E., Martin R. J., Lefevre M., Cefalu W. T., Ye J., Butyrate improves insulin sensitivity and increases energy expenditure in mice. Diabetes. 58: 1509-1517, 2009.
3. Donohoe D. R., Garge N., Zhang X., Sun W., O'Connell T. M., Bunger M. K., Bultman S. J., The microbiome and butyrate regulate energy metabolism and autophagy in the mammalian colon. Cell Metab. 13: 517-526, 2011.
4. Blouin J. M., Penot G., Collinet M., Nacfer M., Forest C., Laurent-Puig P., Coumoul X., Barouki R., Benelli C., Bortoli S., Butyrate elicits a metabolic switch in human colon cancer cells by targeting the pyruvate dehydrogenase complex. Int. J. Cancer. 128: 2591-2601, 2011.
5. Scharlau D., Borowicki A., Habermann N., Hofmann T., Klenow S., Miene C., Munjal U., Stein K., Glei M., Mechanisms of primary cancer prevention by butyrate and other products formed during gut flora-mediated fermentation of dietary fibre. Mutat. Res. 682: 39-53, 2009.

6. Tang Y., Chen Y., Jiang H., Robbins G. T., Nie D., G-protein-coupled receptor for short-chain fatty acids suppresses colon cancer. Int. J. Cancer. 128: 847-856, 2011.
7. Hamer H. M., Jonkers D., Venema K., Vanhoutvin S., Troost F. J., Brummer R. J., Review article: the role of butyrate on colonic function. Aliment. Pharmacol. Ther. 27: 104-119, 2008
8. Binder H. J. 2010. Role of colonic short-chain fatty acid transport in diarrhea. Annu. Rev. Physiol. 72: 297-313.
9. Harig J. M., Soergel K. H., Komorowski R. A., Wood C. M., Treatment of diversion colitis with short-chain-fatty acid irrigation. N. Engl. J. Med. 320: 23-28, 1989.
10. Breuer R. I., Buto S. K., Christ M. L., Bean J., Vernia P., Paoluzi P., Di Paolo M. C., Caprilli R., Rectal irrigation with short-chain fatty acids for distal ulcerative colitis. Preliminary report. Dig. Dis. Sci. 36: 185-187, 1991.
11. Vernia P., Marcheggiano A., Caprilli R., Frieri G., Corrao G., Valpiani D., Di Paolo M. C., Paoluzi P., Torsoli A., Short-chain fatty acid topical treatment in distal ulcerative colitis. Aliment. Pharmacol. Ther. 9: 309-313, 1995.
12. Scheppach W., Treatment of distal ulcerative colitis with short-chain fatty acid enemas. A placebo-controlled trial. German-Austrian SCFA Study Group. Dig. Dis. Sci. 41: 2254-2259, 1996.
13. Di Sabatino A., Morera R., Ciccocioppo R., Cazzola P., Gotti S., Tinozzi F. P., Tinozzi S., Corazza G. R., Oral butyrate for mildly to moderately active Crohn's disease. Aliment. Pharmacol. Ther. 22: 789-794, 2005.
14. WO 1996/014577
15. WO 1996/036239
16. WO 2002/019832
17. WO 2014/193248
18. WO 2015/005804
19. WO 2015/026245

The invention claimed is:

1. A method of increasing levels of short chain fatty acids produced by microbiota in the gut of a subject in need thereof, the method comprising administering to the subject a composition containing beta-casein, wherein at least 95% by weight of the beta-casein is beta-casein A2, and wherein the short chain fatty acid is selected from the group consisting of acetic acid and butanoic acid.

2. The method as claimed in claim 1, wherein the beta-casein comprises 100% by weight A2 beta-casein.

3. The method as claimed in claim 1, wherein the gut microbiota is selected from the genera *Bifidobacterium, Bacteroides, Clostridium*, and *Ruminococcus*.

4. The method as claimed in claim 1, wherein the composition is milk or a milk product.

5. The method as claimed in claim 4, wherein the milk is fresh milk, milk powder, liquid milk reconstituted from powder, skim milk, infant formula, homogenised milk, condensed milk, evaporated milk, pasteurised milk, or non-pasteurised milk.

6. The method as claimed in claim 4, wherein the milk product is cream, yoghurt, quark, cheese, butter, or ice cream.

7. The method as claimed in claim 1, wherein the subject is a human.

* * * * *